(12) United States Patent
McDonough et al.

(10) Patent No.: US 8,987,496 B1
(45) Date of Patent: Mar. 24, 2015

(54) POINT OF USE GENERATION OF AMYL NITRITE

(71) Applicant: Southwest Research Institute, San Antonio, TX (US)

(72) Inventors: Joseph A. McDonough, Helotes, TX (US); Darrel W. Johnston, Boerne, TX (US); Paul M. Thompson, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 14/054,194

(22) Filed: Oct. 15, 2013

(51) Int. Cl.
| C07C 203/04 | (2006.01) |
| C07C 203/00 | (2006.01) |
| C07C 201/04 | (2006.01) |
| A61M 5/19 | (2006.01) |

(52) U.S. Cl.
CPC .............. *C07C 201/04* (2013.01); *A61M 5/19* (2013.01)
USPC ........................................................ 558/488

(58) Field of Classification Search
CPC combination set(s) only.
See application file for complete search history.

(56) References Cited

U.S. PATENT DOCUMENTS

| 2,927,939 | A | | 3/1960 | Yunker, Jr. et al. |
| 3,106,511 | A | | 10/1963 | Cuttler et al. |
| 4,309,303 | A | | 1/1982 | Boyce |
| 4,980,496 | A | * | 12/1990 | Fruchey ........................ 558/488 |
| 8,476,469 | B2 | * | 7/2013 | Liu et al. ........................ 558/488 |
| 8,722,918 | B2 | * | 5/2014 | Liu et al. ........................ 558/488 |
| 2003/0149292 | A1 | | 8/2003 | Karrer et al. |

OTHER PUBLICATIONS

S.I. Baskin, et al, "Cyanide Poisoning", Medical Aspects of Chemical and Biological Warfare, Walter Reed Army Medical Center, Washington, D.C., 1997, Chapter 10, pp. 271-286.
K. Mathes, et al, "The Determination of Methaemoblobin and Cyanomethaemoglobin in Circulating Blood", Naunyn-Schmiedebergs Arch. Exp. Pathol. Pharmakol., 1939, 191; pp. 706-714 (English translation not available).

\* cited by examiner

*Primary Examiner* — Nyeemah A Grazier
(74) *Attorney, Agent, or Firm* — Tucker Grossman et al.

(57) ABSTRACT

The present disclosure relates to devices and methods for the preparation of amyl nitrite formulations at a point of use location from relatively shelf-stable reagents employing acidic cationic exchange resins.

19 Claims, 2 Drawing Sheets

POINT OF USE GENERATION OF AMYL NITRITE

GOVERNMENT FUNDING

This invention was made with United States Government support under Contract No. HHSO100201100038C awarded by the Department of Health and Human Services, Assistant Secretary for Preparedness and Readiness, Office of Acquisitions Management, Contracts and Grants. The Government has certain rights in this invention.

FIELD OF THE INVENTION

This disclosure relates to the preparation of amyl nitrite formulations at point of use from relatively shelf stable reagents, employing acidic cationic exchange resins. The amyl nitrite so produced may be used as an antidote for cyanide and/or hydrogen sulfide poisoning as well as high blood pressure.

BACKGROUND

Amyl nitrite ($C_5H_{11}ONO$) is a known vasodilator and expands blood vessel to lower blood pressure. It is therefore employed to treat heart disease and angina. In addition, amyl nitrite is used as an antidote for cyanide poisoning where it acts as an oxidant to induce the formation of methemoglobin which in turn can attenuate cyanide as cyanomethemoglobin. The alkyl group is generally unreactive and the chemical and biological properties are primarily due to the nitrite (ONO) group.

U.S. Pat. No. 3,106,511 relates to medicament compositions containing amyl nitrite and to their preparation and use. U.S. Pat. No. 4,309,303 relates to a method of stabilizing liquid alkyl nitrites by adding ethyl hydroxyethyl cellulose, calcium silicate and mixtures thereof and mixing to produce solid state compositions and to stabilize compositions thereof. U.S. Patent Publication No. 2003/0149292 relates to the continuous synthesis of alkyl nitrites by reacting an alcohol with an inorganic nitrite in an acidic medium.

However, amyl nitrite's utility as a field antidote treatment remains limited by its drug product stability characteristics (presently 2 year storage at 2-8° C. and limited storage at 25° C.). It is also known that amyl nitrite is unstable unless protected for oxygen and light. Thus, even with stabilization it cannot be left unprotected for relatively long periods of time.

In addition, amyl nitrite is administered by nasal inhalation, which makes it difficult to determine dose level and the amount of amyl nitrite that is delivered (as measured by blood methemoglobin concentration) is relatively low. Additionally, due to unknown dose delivery, there has been no dose to efficacy or dose to safety relationship established.

It is also useful to note that amyl nitrite is a relatively low viscosity and volatile fluid with a boiling point of 97-99° C. As noted, it is typically employed in drug form by inhalation of vapors of the liquid. Accordingly, the relative high volatility will separately reduce the efficacy of a dose through evaporation away from the target zone or uncontrolled release.

SUMMARY

A method for preparing amyl nitrites of the formula $C_5H_{11}ONO$ comprising forming a mixture of amyl alcohol of the formula $C_5H_{11}OH$ with a nitrite of the formula $MNO_2$ in an aqueous medium wherein M represents a metal cation selected from an alkali metal or alkali earth metal. The mixture may then be exposed to an acidic cationic exchange resin which results in the formation of amyl nitrite.

In addition, the present disclosure relates to a method for the administration of amyl nitrite wherein one supplies a first sealed compartment which contains amyl alcohol ($C_5H_{11}OH$), a second sealed compartment which contains nitrite of the formula $MNO_2$ in an aqueous medium wherein M represents a metal cation selected from an alkali metal or alkali earth metal; and a third sealed compartment which contains an acidic cationic exchange resin. The first and second sealed compartments are opened and the amyl alcohol and the nitrite are introduced into the third sealed compartment and the amyl alcohol is converted to amyl nitrite ($C_5H_{11}ONO$). The method may be employed for the treatment of cyanide poisoning and/or $H_2S$ poisoning in a human or animal.

Finally, the present disclosure relates to a device for delivery of amyl nitrite. The device comprises a first sealed compartment which contains amyl alcohol ($C_5H_{11}OH$), a second sealed compartment which contains nitrite of the formula $MNO_2$ in an aqueous medium wherein M represents a metal cation selected from an alkali metal or alkali earth metal, and a third sealed compartment which contains an acidic cationic exchange resin.

As discussed more fully herein, the above device and associated methods offer a procedure to now produce amyl nitrite from stable reagents at the time of desired administration of amyl nitrite to a selected patient. Accordingly, a shelf-stable point of use protocol is now disclosed and provided for therapeutic amyl nitrite administration.

FIGURES

The above mentioned and other features of this disclosure, and the manner of attaining them, will become more apparent and better understood by reference to the following description of embodiments described herein taken in conjunction with the accompanying drawings, wherein.

DETAILED DESCRIPTION

Figure 1:
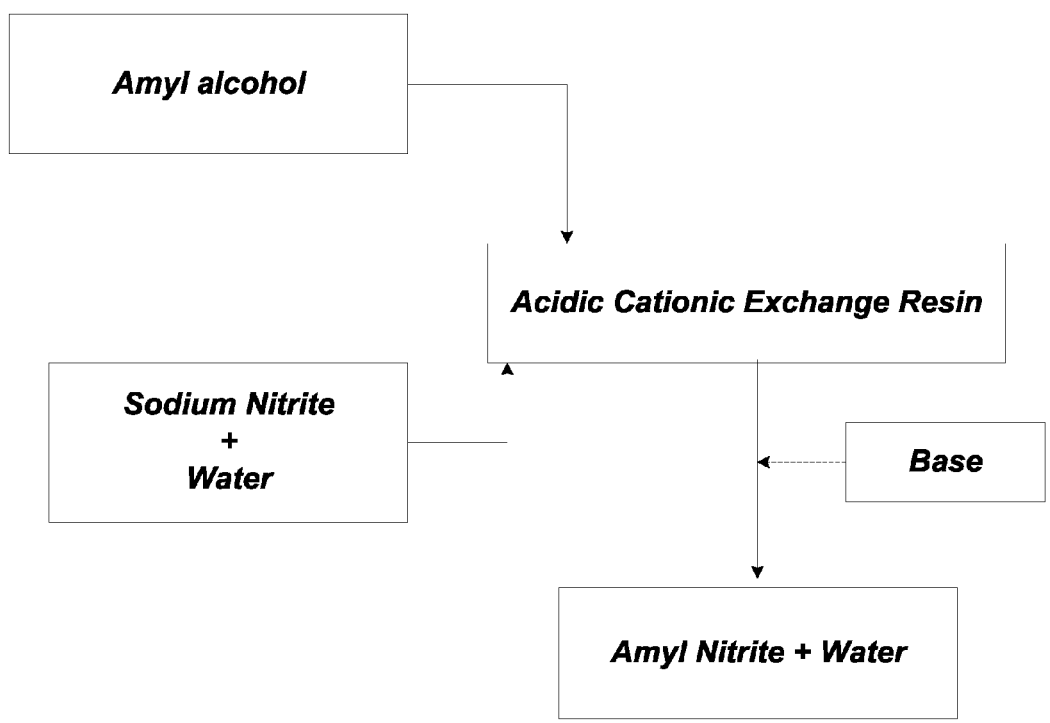
FIG. 1 illustrates a schematic diagram for a point of use generation of amyl nitrite employing an acidic cationic exchange resin.

It may be appreciated that the present disclosure is not limited in its application to the details of construction and arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

As noted, the present disclosure provides for the preparation of amyl nitrite when needed for use and such that it is conveniently available for a point-of-use application. Amyl nitrite is a chemical compound with the formula $C_5H_{11}ONO$. A variety of isomers are known which all feature the amyl group attached to the nitrite functional group. One common form of amyl nitrite includes isoamyl nitrite of the formula $(CH_3)_2CHCH_2CH_2ONO$. This is otherwise known as 3-methylbutyl nitrite.

Preparation of amyl nitrite involves the reaction of amyl alcohol (any alcohol with the formula $C_5H_{11}OH$) with nitrous acid where the nitrous acid is formed in situ via the reaction of sulfuric acid with sodium nitrite:

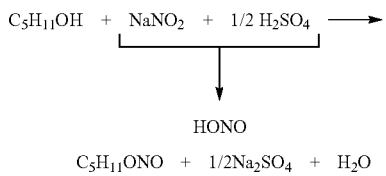

It has now been found that an acidic cation exchange resin may now be employed which resin replaces the sulfuric acid as a component for amyl nitrite formation. Accordingly, one now has the ability to package the reagents (amyl alcohol, alkali metal nitrite, water, cation exchange resin) to provide a shelf-stable system that synthesizes amyl nitrite as needed at a desired location. The alkali metal nitrite that may be employed or $MNO_2$ includes that situation where M is any alkali metal cation (e.g. lithium, sodium or potassium) or alkaline-earth metal cation (e.g. magnesium, calcium). For example, M may preferably include $Na^+$, $Li^+$, or $Ca^+$.

An acidic cation exchange resin herein may be understood as an insoluble organic polymer resin having negatively charged radicals attached to it that can attract and hold $H^+$ in surrounding solution. The $H^+$ is then subsequently exchanged with $M^+$ (e.g. $Na^+$) during the point-of-use preparation of the amyl nitrate. In such context, the acidic cation exchange resin replaces the use of sulfuric acid in the reaction noted above, where $H^+$[Polymer Resin] represents an acidic cation exchange resin:

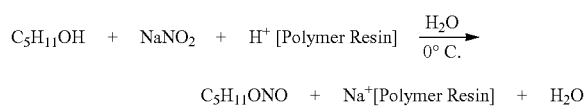

One preferred acidic cationic exchange resin includes a sulfonic acid resin that contains a backbone chain of polymer prepared from polymerization of a mixture of styrene monomer and divinylbenzene which is then treated with sulfuric acid to provide the acidic cationic exchange resin of the following general structure (where the crosslinks due to the presence of polymerized divinylbenzene are not shown for clarity):

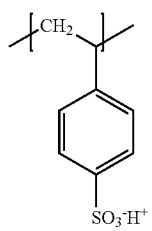

Accordingly, in preferred embodiment, the preparation of amyl nitrite herein may proceed as follows:

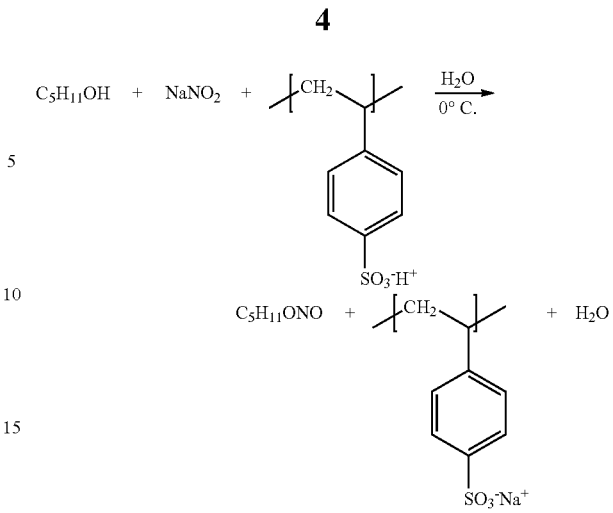

One particularly preferred acidic cationic exchange resin is available from Dow Chemical Company and amounts to a DOWEX™ 50W resin that as noted above, contains polystyrene and poly(vinyl benzene) wherein the level of divinylbenzene may vary between 2% to 8%. In addition, the mesh size may vary from 50-400 and the water retention may vary from 50-82%.

The total exchange capacity may also vary from 0.6-1.7 meq/mL. The resins also indicate a density in the range of 46-50 lbs/ft$^3$.

As alluded to above, the amyl nitrite prepared herein using an acidic cationic exchange resin may include n-alkyl amyl nitrite ($CH_3(CH_2)_4ONO$) as well as 2-methylbutyl nitrite ($CH_3CH_2CH(CH_3)CH_2ONO$) and/or 3-methylbutyl nitrite (($CH_3)_2CHCH_2CH_2ONO$). Such nitrite compounds may all be conveniently prepared for point of use application herein from their corresponding alcohols. For example, 2-methylbutyl nitrite may be prepared from 2-methylbutyl alcohol and 3-methylbutyl nitrite may be prepared from 3-methylbutyl alcohol. In addition, one may produce a mixture of the 2-methylbutyl nitrite and 3-methyl-butyl nitrite, wherein the 3-methylbutyl nitrite is present at a level of 90% by weight or greater, and in particular, at a level of 91%, 92%, 93%, 94%, 95%, 96%, 97%, 98% and 99% by weight. More preferably, a mixture of 2-methylbutyl nitrite and 3-methyl butyl nitrite may be produced, wherein the level of 3-methyl butyl nitrite is at a level of 98% by weight or greater.

It is worth noting that upon combination of the amyl alcohol, metal nitrite/water and exposure to the acidic cationic exchange resin, amyl nitrite is produced and the remaining components after mixing and reacting include water, the alkali metal form of the acidic cationic exchange resin and any remaining amyl alcohol. These are relatively innocuous and therefore have no adverse influence on the point of use generation of amyl nitrite for therapeutic purposes.

FIG. 1 now illustrates one convenient method herein of producing amyl nitrite for a point of use application. As shown, one may now, in a field deployable apparatus, with stability for a period of 1-3 years, isolate amyl nitrite, sodium nitrite and water and the acidic cationic exchange resin. Such may be conveniently achieved by placement of the selected amyl alcohol and mixture of sodium nitrite and water in break-seal ampoules which can be broken by the user to allow for the indicated flow of reagents into the acidic cationic exchange resin compartment. Reference to break-seal ampoules may be generally understood as any sort of sealed containment compartment which contains and preserves the identified reagent. Such sealed compartments may have a volume of 0.1-1000 ml. The produced amyl nitrite can then be delivered to the user that would preferably make the amyl nitrite available for inhalation. This could be achieved by placement of cloth at the amyl nitrite output location which would then provide amyl nitrite vapors.

It is contemplated herein that the device indicated in FIG. 1 may, as shown, optionally include the ability to treat the amyl nitrite output with a base (e.g. a metal carbonate ($MCO_3^{2-}$) or metal bicarbonate ($MHCO_3^-$)). This in turn will assist in neutralizing any nitrous acid ($HNO_2$) formation.

Figure 2:
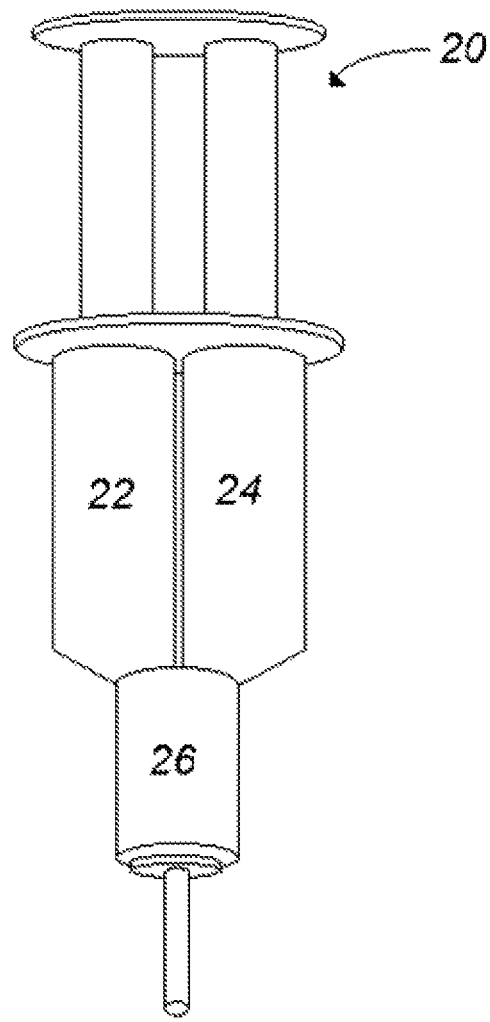
FIG. 2 illustrates a syringe for providing point of use generation of amyl nitrite employing an acidic cationic exchange resin.

With attention next directed to FIG. 2, the point of use delivery of amyl nitrite herein may also be conveniently provided via a syringe 20. A syringe may be broadly understood herein as a device that includes a plunger that fits within a containment sections (e.g. a tube) allowing the syringe to expel a liquid (amyl nitrite) through an opening (orifice). Specifically, the syringe may contain compartment 22 which contains amyl alcohol, compartment 24 which contains sodium nitrite and water, and compartment 26 which contains the acidic cationic exchange resin. Upon compression of the syringe the compartments 22 and 24 can release and introduce the amyl alcohol in mixture with the sodium nitrite and water to the acidic cationic exchange resin, which will then convert the amyl alcohol and deliver a required amount of amyl nitrite. Compartments 22, 24 and 26 may all be sealed and therefore provide an indefinite shelf life for the syringe device for a selected field application. Compartment 22, 24, and 26 may each be of a size suitable to accommodate 1-500 ml of reagent. Accordingly, the syringe herein may have a capacity of 3 ml to 1500 ml of reagent as may be necessary for the delivery of amyl nitrite compound.

It is also contemplated herein that the acidic cationic exchange resin noted above may be conveniently replaced with a Lewis Acid reagent. Reference to a Lewis Acid is reference to an acid compound which is an electron pair acceptor. An example of a Lewis Acid contemplated for use herein is $BF_3$

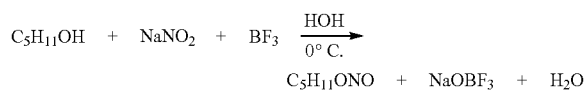

$$C_5H_{11}OH + NaNO_2 + BF_3 \xrightarrow[0°C.]{HOH} C_5H_{11}ONO + NaOBF_3 + H_2O$$

WORKING EXAMPLES

Acidic Cationic Exchange Resin Catalyzed Synthesis of 3-Methyl Butyl Nitrite

On a coarse Buchner frit was conditioned 300 mL DOWEX 50WX4-50 acidic cationic exchange resin by rinsing with 100 ml DI water, 200 ml methanol and 1000 ml D water. The proton form of the resin was assured by rinsing with 250 ml 10% v/v H2SO4 in DI water followed by 2000 ml DI water. Rinse same pH to paper as DI water.

A 2 L three-neck round bottom flask was flushed with $N_2$ and outfitted with a magnetic stirrer and internal temperature monitoring equipment and an addition funnel modified for subsurface addition. The flask was charged with the conditioned acidic cationic exchange resin (300 ml, 330 meq), 200 ml DI water and 3-methyl butanol (22 g, 250 mmol). A solution of sodium nitrite was prepared (21 g, 304 mmol) by dissolving the salt up to 150 ml with DI water. The sodium nitrite solution was added to the modified addition funnel. The reactor was cooled to a temperature of about −1° C. to 1° C. The reaction was carried out under a $N_2$ blanket. The reactor was allowed to warm to 20° C. under $N_2$ with stirring for 2 hours. Upon opening of the reactor a red brown gas was observed. The inhomogeneous mixture of resin, aqueous and organic components was filtered through a coarse Buchner frit to remove resin facilitating transfer with a minimum of DI water. The aqueous phase was saturated with 25 g of sodium chloride and the phases were separated. The organic phase was washed with 25 ml of 4% potassium carbonate in water. An organic yellow product was dried with about 400 mg of anhydrous potassium carbonate. The final product was 3-methyl butyl nitrite (9.3 g, 79.2 mmol) produced in 32% yield. Proton NMR confirmed the 3-methyl butyl nitrite formation with 2% 3-methyl butanol remaining. $^1$H NMR (400 MHz, CdCl$_3$, δ) 4.75 (m, 2H, —CH$_2$—ONO) 2.75 (m 2H, —CH$_2$—CH$_2$—ONO), 2.63 (m, 1H, —CH(CH$_3$)$_2$), 0.93 (d, 6H, —CH(CH$_3$)).

Acidic Cationic Resin Synthesis of 3-Methyl Butyl Nitrite at Room Temperature

On a coarse Buchner frit was conditioned 30 ml of DOWEX 50WX-50 acidic cationic exchange resin by rinsing with 300 ml DI water, 50 ml methanol and 300 ml DI water. The proton form of the resin was assured by rinsing with 30 ml 10% v/v H$_2$SO$_4$ in DI water then 500 ml DI water. Rinse same pH to paper as DI water.

A round bottom flask was charged with resin, 3-methyl butanol (AA)(2.0 g, 23 mmol) and 20 ml DI water. Open to the atmosphere and without stirring, at room temperature, was added sodium nitrite (2 g, 29 mmol). Some warming and bubbling was observed. The flask was allowed to stand open to air for 20 minutes. The resin was removed by filtration on a coarse Buchner frit. Phases then separated. Retained 1.1 g crude organic product shown to be 76.9% 3-methyl butyl nitrite with AA starting material. 42.3% crude yield or 32.5% yield of 3-methyl butyl nitrite adjusted for purity. $^1$H NMR (400 MHz, CdCl$_3$, δ) 4.75 (m, 2H, —CH$_2$—ONO), 2.75 (m, 2H, —CH$_2$—CH$_2$—ONO), 2.63 (m, 1H, —CH(CH$_3$)$_2$), 0.93 (d, 6H, —CHCH$_3$).

As may now be appreciated, the present disclosure provides a convenient method to produce amyl nitrite from stable reagents at time of administration which minimizes stability issues involved with direct delivery of amyl nitrite protocols. Amyl nitrite is now produced by the reaction of amyl alcohol with metal nitrite in water catalyzed by an acidic cationic exchange resin. The resin acts in place of aqueous acid as a non-irritating component. The delivery methods and devices of the present disclosure are suitable for use in a variety of field conditions, including but not limited to relatively high temperatures (30° C.-45° C.) such as what may be encountered in a desert environment and for periods extending up to 1-3 years. That is, the reagents (amyl alcohol and metal nitrite) and the acidic cationic exchange resin are preserved in sealed condition and remain active and suitable for mixing and reacting with the acidic cationic exchange resin to provide a point of use antidote for cyanide and/or hydrogen sulfide poisoning as well as high blood pressure.

The invention claimed is:

1. A method for preparing amyl nitrites of the formula $C_5H_{11}ONO$ comprising:
    forming a mixture of amyl alcohol of the formula $C_5H_{11}OH$ with a nitrite of the formula $MNO_2$ in an aqueous medium wherein M represents a metal cation selected from an alkali metal or alkali earth metal;
    exposing said mixture to an acidic cationic exchange resin and forming amyl nitrite.

2. The method of claim 1 wherein said acidic cationic exchange resin comprises a sulfonic acid resin comprising a polymer formed from polymerization of the mixture of styrene monomer and divinylbenzene and having the structure:

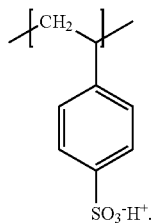

3. The method of claim 1 wherein said amyl alcohol comprises 3-methyl butyl alcohol.

4. The method of claim 3 wherein said amyl nitrite comprises 3-methyl butyl nitrite.

5. The method of claim 1 wherein said nitrite of the formula $MNO_2$ comprises $NaNO_2$.

6. The method of claim 1 wherein said amyl nitrite is exposed to a base to neutralize nitrous acid ($HNO_2$).

7. A method for the administration of amyl nitrite comprising:
supplying a first sealed compartment which contains amyl alcohol ($C_5H_{11}OH$), a second sealed compartment which contains nitrite of the formula $MNO_2$ in an aqueous medium wherein M represents a metal cation selected from an alkali metal or alkali earth metal; and a third sealed compartment which contains an acidic cationic exchange resin;
wherein said first and second sealed compartments are opened and said amyl alcohol and said nitrite are introduced into said third sealed compartment and said amyl alcohol is converted to amyl nitrite ($C_5H_{11}ONO$).

8. The method of claim 7 wherein said acidic cationic exchange resin comprises a sulfonic acid resin comprising a polymer formed from polymerization of the mixture of styrene monomer and divinylbenzene and having the structure:

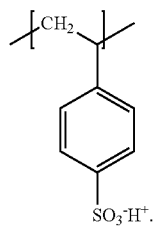

9. The method of claim 7 wherein said amyl alcohol comprises 3-methyl butyl alcohol.

10. The method of claim 9 wherein said amyl nitrite comprises 3-methyl butyl nitrite.

11. The method of claim 7 wherein said nitrite of the formula $MNO_2$ comprises $NaNO_2$.

12. The method of claim 7 wherein said device comprises a syringe.

13. The method of claim 7 wherein said sealed compartments comprise ampoules.

14. The method of claim 7 wherein said method is employed for treatment of cyanide poisoning.

15. The method of claim 7 wherein said method is employed for treatment of $H_2S$ poisoning.

16. A device for the delivery of amyl nitrite comprising:
a. a first sealed compartment containing which contains amyl alcohol ($C_5H_{11}OH$)
b. a second sealed compartment which contains nitrite of the formula $MNO_2$ in an aqueous medium wherein M represents a metal cation selected from an alkali metal or alkali earth metal; and
c. a third sealed compartment which contains an acidic cationic exchange resin.

17. The device of claim 14 wherein said device comprises a syringe.

18. The device of claim 14 wherein said amyl alcohol comprises 3-methyl butyl alcohol.

19. The device of claim 14 wherein said nitrite of the formula $MNO_2$ comprises $NaNO_2$.

* * * * *